(12) United States Patent
Nohta et al.

(10) Patent No.: US 6,333,199 B1
(45) Date of Patent: Dec. 25, 2001

(54) METHOD OF ANALYZING BISPHENOLS AND POLYPHENOLS

(75) Inventors: Hitoshi Nohta; Hideyuki Yoshida; Masatoshi Yamaguchi, all of Fukuoka (JP)

(73) Assignee: Laboratory of Molecular Biophotonics, Hamakita (JP)

( * ) Notice: Subject to any disclaimer, the term of this patent is extended or adjusted under 35 U.S.C. 154(b) by 0 days.

(21) Appl. No.: 09/458,653

(22) Filed: Dec. 10, 1999

(51) Int. Cl.$^7$ ................................................ G01N 33/00
(52) U.S. Cl. ....................... 436/131; 436/56; 436/140; 436/172; 436/422; 436/82.08
(58) Field of Search ............................ 436/131, 56, 139, 436/140, 164, 166, 171, 172; 422/52, 68.1, 82.05, 82.08

(56) References Cited

PUBLICATIONS

Boileau et al. "End–to–End Cyclization Dynamics of a Pyrene End–Capped (Bisphenol A–diethylene glycol) Polycarbonate", Polym. Prep. (Am. Chem. Soc.), 1988, v.29 (1), pp. 509–510.*

Boileau et al. "End–to–End Cyclization of a Pyrene End–Capped Polycbisphenol AF–diethylene glycol carbonate)", Macromolecules, 1989, v. 22, pp. 215–220.*

Duhamel et al. "End–to–End Cyclization of a Pyrene End–Capped Poly(bisphenol AF–diethylene glycol carbonate) in Solution", Eur. Polym. J., 1994, v. 30, No. 1, pp. 129–134.*

Wilken et al. "End–Group Dynamics of Fluorescently Labeled Dendrimers", Macromol. Rapid Commun., 1997, v. 18, No. 8, pp. 659–665 (Abstract).*

Fleet et al. "Application of Electroluminescence Techniques to the Determination of Aromatic Hydrocarbons", Talanta, 1968, v. 15, pp. 566–570.*

Taylor et al. "Excitation Resolved Synchronous Fluorescence Analysis of Aromatic Aompounds and Fuel Oil", Anal. Chem. 1987, v. 59, pp. 2180–2187.*

Narita et al. Fluorescent Molecular Sensory System Based on bis Pyrene–Modified γ–Cyclodextrin Dimer for Steroids and Endocrine Disruptors, Anal. Sci., 2001, v. 17, No. 3, pp. 379–385 (Abstract).*

Koiso et al., "Development of Precolumn HPLC–Excimer Fluorescence Detection of Polyamine", The 118$^{th}$ Annaul Meeting of the Pharmaceutical Society of Japan, Mar. 31 to Apr. 2, 1998.

Satozono et al., "Sensitive Detection of Polyamine Compounds by the Intramolecular Excimer Labeling Technique" (Abstract), VIIIth International Symposium on Luminescence Spectrometry in Biomedical and Environmental Analysis–Detection Techniques and Applications in Chromatography and Capillary Electrophoresis, Spain, May 26–29, 1998.

Sonoda et al., "Highly Selective and Highly Sensitive HPLC Quantitative Analyzing of Dicarboxylic Acids by Excimer Fluorescence Derivatization", The 47$^{th}$ Annual Meeting of Japan Society of Analytical Chemistry, Oct. 6–8, 1998.

(List continued on next page.)

*Primary Examiner*—Jill Warden
*Assistant Examiner*—Meline Gakh
(74) *Attorney, Agent, or Firm*—Leydig, Voit & Mayer, Ltd.

(57) ABSTRACT

The method of analyzing polyphenols and bisphenols in accordance with the present invention comprises a step of reacting a bisphenol and/or a polyphenol with a labeling reagent having a pyrene group, so as to generate a fluorescent derivative; a step of irradiating the fluorescent derivative with excitation light and detecting fluorescence emitted from the fluorescent derivative; and a step of calculating an amount of the bisphenol and/or polyphenol in a test sample according to an intensity of thus detected fluorescence and a relationship between a known concentration of a bisphenol and/or a polyphenol contained in a standard sample and fluorescence intensity.

8 Claims, 5 Drawing Sheets

OTHER PUBLICATIONS

Koiso et al., "Development of Highly Sensitive HPLC Quantitative Analysis of Polyamines by Excimer Fluorescence Derivation", The 15$^{th}$ Conference of Kyushu Branch of Pharmaceutical Society of Japan, 1998.

Yoshida et al., "Highly Sensitive and Highly Selective Quantitative Analysis of Lysine and Ornithine by Excimer Fluorescence Derivatization–HPLC", The 119$^{th}$ Annaul Meeting of the Pharmaceutical Society of Japan, Mar. 29–31, 1999.

Yosida et al., "Highly Selective and Highly Sensitive Quantitative Analysis of Dicarboxylic Acids by Excimer Fluorescence Derivatization (2)", The 60$^{th}$ Symposium on Analytical Chemistry, May 15–16, 1999.

Yoshida et al., "Excimer–fluorescence Derivatization HPLC Methods for Biogenic Component Analysis", Chromatography, vol. 20, No. 2, Proceedings on the 6$^{th}$ Chromatography Symposium on Development of Effective Pre–treatment and its Application, Jun. 25–26, 1999.

Harada et al., "Development of Highly Sensitive and Highly Selective HPLC Quantitative Analysis of Polyamine by Excimer Fluorescence Derivatization", The 36$^{th}$ Joint Conference of Kyushu Branches of Societies Related to Chemistry, Jul. 9, 1999.

Harada et al., "Development of Detection of Dicarboxylic Acids in Human Urine by Excimer Fluorescence Derivatization, and Method for Simply Diagnosing Glutaric Acid Urine Symptom (1)", Thirteenth Symposium on Analytical Chemistry of Biological Substances, Aug. 19–20, 1999.

Nakano et al., "Development of HPLC–Excimer Fluorescence Quantitative Analysis of Agent for Treating Wilson's Disease", The 48$^{th}$ Annual Meeting of Japan Society for Analytical Chemistry, Sep. 8–10, 1999.

Harata et al., "Development of Highly Selective Quantitative Analysis of Bisphenols by Excimer Fluorescence Derivatization", The 16$^{th}$ Conference of Kyushu Branch, The Pharmaceutical Society of Japan (1999).

* cited by examiner

METHOD OF ANALYZING BISPHENOLS AND POLYPHENOLS

BACKGROUND OF THE INVENTION

1. Field of the Invention

The present invention relates to a method of analyzing bisphenols and polyphenols; and, in particular, to a method of analyzing a bisphenol and/or a polyphenol having at least two phenolic hydroxyl groups contained in a test sample.

2. Related Background Art

Bisphenols are used in large amounts as materials (stabilizer, plasticizer, and the like) for polycarbonate resins, phenol resins, and the like in familiar everyday goods and the like. It has recently been reported that bisphenols leak into the environment from such everyday goods or wastes thereof, so that attention is being paid to their distribution in the environment, their influences on the ecosystem, their toxicity to humans, and so forth. It has also been indicated that bisphenols may be one of exogenous endocrine disrupting chemicals, but there are still many unclear points concerning their actions on organisms and their mechanism. One of the reasons behind this unclearness is attributable to the imperfection in the method of analyzing bisphenols. Conventionally, gas chromatography/mass spectrometry (GC/MS) method, liquid chromatography/mass spectrometry (LC/MS) method, and LC/fluorescence detection method have been used in general as the method of analyzing bisphenols.

SUMMARY OF THE INVENTION

As a result of repeated diligent studies, the inventors have found that the following problems exist in the above-mentioned conventional analyzing methods.

1) Though the GC/MS and LC/MS methods have a high selectivity, their preprocessing operations are complicated, and their apparatus cost and running cost are so high that it tends to be difficult for them to be used for the routine analysis of a number of test samples (specimens).

2) The LC/fluorescence detection method is a method in which the phenolic hydroxyl groups of bisphenols are fluorescence-labeled with a fluorescent reagent such as dansyl chloride or the like, and their fluorescence is detected, whereby both of its apparatus cost and running cost are relatively inexpensive. In this method, however, many monophenols and amines are also fluorescence-labeled. As a result, background fluorescence enhances, the selectivity for bisphenols is lower, and a sufficient sensitivity may not be obtained, whereby it is not suitable for analyzing bisphenols in the environment.

3) While simple kits for analyzing bisphenol A (e.g., ELISA Kit manufactured by Takeda Chemical Industries, Ltd.) are commercially available, they include many compounds which generate a crossing reaction, whereby they are only applicable to limited samples and are problematic in that their preprocessing is complicated.

In view of such circumstances, it is an object of the present invention to provide a simple method of analyzing bisphenols and polyphenols, which can analyze bisphenols and/or polyphenols with a high sensitivity and a high selectivity without necessitating complicated preprocessing.

The inventors have repeated diligent studies in order to achieve the above-mentioned object, and have found that, when a labeling reagent having a pyrene group is caused to act on and label at least two phenolic hydroxyl groups in a molecule of a bisphenol or a polyphenol, and thus labeled compound is optically excited, an intramolecular excimer is formed, so that fluorescence having a wavelength specific to this excimer is quantitatively emitted, whereby the present invention is accomplished.

Namely, the method of analyzing bisphenols and polyphenols in accordance with the present invention is a method of analyzing a polyphenol and/or a bisphenol having at least two phenolic hydroxyl groups contained in a test sample, the method comprising a step of reacting a bisphenol and/or a polyphenol with a labeling reagent having a pyrene group, so as to generate a fluorescent derivative; a step of irradiating the fluorescent derivative with excitation light and detecting fluorescence emitted from the fluorescent derivative; a step of calculating an amount of the bisphenol and/or polyphenol in the test sample according to thus detected fluorescence intensity and a relationship between a known concentration of a bisphenol and/or a polyphenol contained in a standard sample and fluorescence intensity.

In such a method of analyzing bisphenols and polyphenols, the labeling reagent substitutes for hydrogen atoms in the phenolic hydroxyl groups in a molecule of a bisphenol and/or a polyphenol, thereby generating a fluorescent derivative labeled with pyrene groups. When this fluorescent derivative is irradiated with excitation light, the pyrene groups within the molecule are optically excited, and thus excited pyrene groups are dimerized within the molecule, whereby an intramolecular excimer is formed. The intramolecular excimer emits fluorescence having a wavelength different from that of the fluorescence (monomer fluorescence) emitted by the pyrene groups alone upon optical excitation. According to the resulting fluorescence intensity and a relationship (calibration curve or working curve) between the concentration and fluorescence intensity determined concerning a standard sample containing a known concentration of bisphenols and/or polyphenols, or upon addition of the standard sample, for example, the quantity of the bisphenol and/or polyphenol in the test sample is determined.

In the step of detecting fluorescence, it is preferred that fluorescence having a wavelength of 450 to 530 nm be detected. Such a fluorescence wavelength (450 to 530 nm) includes a wavelength region of the fluorescence emitted from the above-mentioned intramolecular excimer of the fluorescent derivative and is longer than the wavelength of the monomer fluorescence emitted from the pyrene group monomer such as one in the labeling reagent or the like. Therefore, the selectivity for bisphenols or polyphenols is enhanced, so as to enable high-sensitivity analysis.

Preferably, as the test sample, one containing an oxyphenyl group at a terminal within its molecule is used, whereby the present invention becomes quite effective. More preferably, a bisphenol is at least one selected from the group consisting of 2,2-bis(4-hydroxyphenyl) propane, 2,2-bis(4-hydroxyphenyl) butane, 4,4'-ethylidene bisphenol, bis(4-hydroxyphenyl) methane, 4,4'-(1-phenylethylidene) bisphenol, and 4,4'-(1,4-phenylene-di-isopropylidene) bisphenol.

Preferably, the method further comprises a step of adding an amine having a polar group, more preferably an amidosulfonic acid, aliphatic amino acid, or amino sugar to the test sample in which the fluorescent derivative is generated. As a consequence, the excess of labeling reagent, which remains within the test sample while being unreacted with a bisphenol or a polyphenol or after hydrolysis, is decomposed. When the separation of components in the test sample by high-performance liquid chromatography (hereinafter referred to as "HPLC") is concurrently used, decomposition products tend to be eluted faster than the labeling reagent itself. Here, the above-mentioned amine is preferably at least one selected from the group consisting of taurine, arginine, γ-aminolactic acid, glucosamine, and mannosamine in particular.

If the labeling reagent having a pyrene group is at least one selected from the group consisting of 4-(1-pyrene) butanoyl chloride, 4-(1-pyrene) pentanoyl chloride, and 4-(1-pyrene) hexanoyl chloride, it will be useful since the efficiency of labeling reaction of bisphenols and/or polyphenols is remarkably enhanced.

DESCRIPTION OF THE PREFERRED EMBODIMENTS

Figure 1:
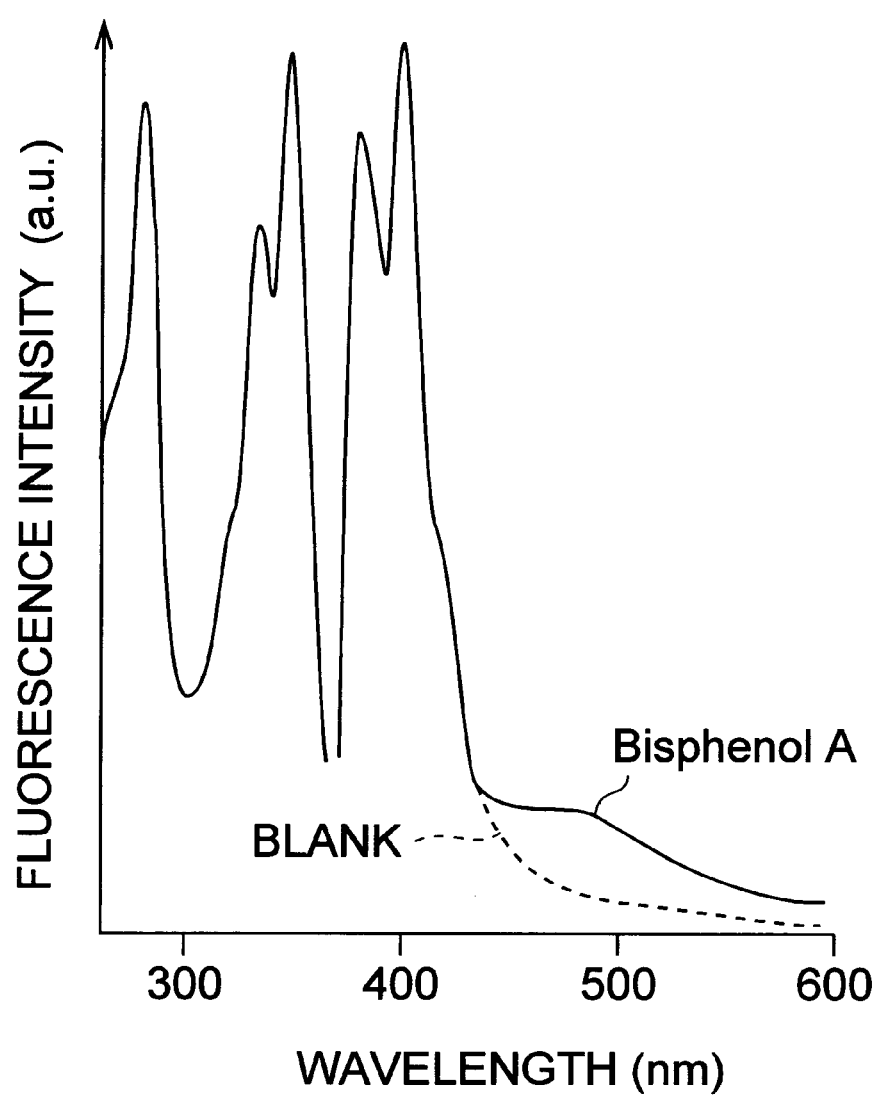
FIG. 1 is a graph showing a fluorescent spectral curve of a test sample solution including a fluorescent derivative corresponding to bisphenol A.

In the following, embodiments of the present invention will be explained in detail. In a preferred embodiment of the method of analyzing bisphenols and polyphenols in accordance with the present invention, first, i) a bisphenol and/or a polyphenol having at least two phenolic hydroxyl groups contained in a test sample are reacted with a labeling reagent having a pyrene group, so as to generate a fluorescent derivative. Subsequently, ii) an amine having a polar group is added to the test sample, so as to decompose the remaining unreacted or hydrolyzed labeling reagent not used for generating the fluorescent derivative. Then, iii) thus obtained fluorescent derivative is irradiated with excitation light, and fluorescence emitted from this fluorescent derivative is detected. Here, the wavelength of fluorescence to be detected is set to 450 to 530 nm, and fluorescence detection signals in this wavelength region detected by a fluorescence detector are integrated, so as to yield a fluorescence intensity.

On the other hand, iv) before analyzing the test sample (actual sample), the above-mentioned steps of i) to iii) are carried out with a standard sample containing a known concentration of a bisphenol or a polyphenol, and a calibration curve is prepared from a relationship between the resulting fluorescence intensity and the concentration. Then, v) according to this calibration curve, the concentration of the bisphenol or polyphenol in the test sample is calculated from the fluorescence intensity of the test sample obtained in the above-mentioned iii).

In the case where a plurality of kinds of bisphenols and/or polyphenols are contained in the test sample in the present invention, vi) a step of introducing the test sample having generated fluorescent derivatives into an HPLC apparatus and separating the fluorescent derivatives corresponding to the respective bisphenols or polyphenols from each other may be carried out. As a consequence, the amounts of respective components can be analyzed individually.

In the following, the test sample, bisphenols, polyphenols, labeling reagent, and amines will be explained individually.

Test Sample

The test sample analyzable by the method of analyzing bisphenols and polyphenols of the present invention is not limited in particular as long as a bisphenol and/or a polyphenol are contained therein, and it may be in the form of solution, semisolid, or solid as long as it has such a concentration that the labeling reaction by the labeling reagent can be carried out with an appropriate solvent. Specific examples thereof include biological samples such as urine sample, blood sample, biological tissues, and the like; and environmental samples such as river water, lake water, seawater, tap water, rainwater, incinerated ash, wastes, animal and plant samples in the environment, their extracts, and the like. Also, there are everyday goods such as various plastic products, contents of canned foods and the like, their extracts, or the like.

Though the preprocessing for the test sample is not limited in particular, it is preferred that various coexisting components be eliminated beforehand, in order to label the phenolic hydroxyl groups of bisphenols and/or polyphenols and carry out fluorescence detection. A specific example of preprocessing is the removal of mixed acidic components or the removal of mixed protein components. The mixed acidic components can easily be removed by normal ion-exchange chromatography.

The removal of mixed protein components, on the other hand, can easily be carried out by a normal method using an acid, an organic solvent, heating, or the like. In particular, since protein components include those exhibiting strong fluorescence, which results in background fluorescence in the method of analyzing bisphenols and polyphenols in accordance with the present invention, the removal of protein components is preferable processing for analyzing bisphenols or polyphenols with a high sensitivity.

Further, components of monophenols or catechins each having only one phenolic hydroxyl group within a molecule may coexist in the test sample. Examples of these monophenols and catechins include phenol, nonylphenol (4-nonylphenol), cresol, naphthol, 3-oxyflavone, and the like. In the method of analyzing bisphenols and polyphenols in accordance with the present invention, these components having only one phenolic hydroxyl group in their molecule are also unselectively labeled by the labeling reaction with the labeling reagent having a pyrene group.

While thus labeled components emit fluorescence (monomer fluorescence) of the pyrene group itself upon optical excitation, no excimer formation is possible within their molecule, whereby they would not emit fluorescence in a longer wavelength region than that in the fluorescence of the pyrene group itself in accordance with the present invention nor the excimer fluorescence due to the intramolecular excimer formation at all. Therefore, the method of analyzing bisphenols and polyphenols in accordance with the present invention is not influenced by the existence of the above-mentioned components having only one phenolic hydroxyl group in their molecule.

Further, in the case where bisphenols and/or polyphenols have a particular structure which cannot exist as a free form in the test sample, the preprocessing preferably comprises the step of decomposing this particular structure by processing including various chemical reactions, so as to liberate bisphenols or polyphenols.

Bisphenols and Polyphenols

Bisphenols to be analyzed in the present invention are not restricted in particular, as long as they are substituted or unsubstituted ones having at least two oxyphenyl groups within their molecule, whereas the oxyphenyl groups may be bonded to terminals of the molecule or inside the molecule other than the terminals. Examples of bisphenols having oxyphenyl groups at terminals of their molecule include those expressed by the following formulas (1) to (6), i.e., 2,2-bis(4-hydroxyphenyl) propane, 2,2-bis(4-hydroxyphenyl) butane, 4,4'-ethylidene bisphenol, bis(4-hydroxyphenyl) methane, 4,4'-(1-phenylethylidene) bisphenol, and 4,4'-(1,4-phenylene-di-isopropylidene) bisphenol.

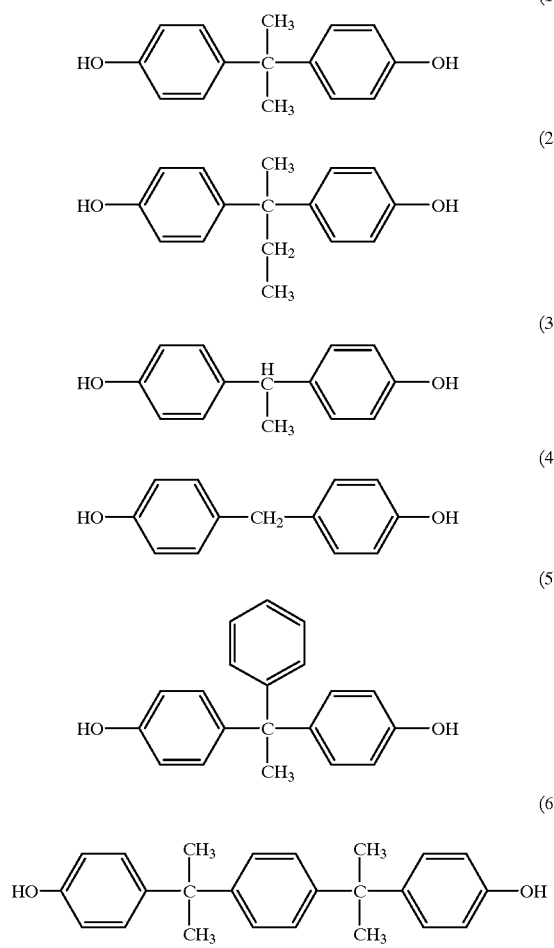

These bisphenols may be contained in the test sample separately or as a mixture of two or more kinds. The method of analyzing bisphenols and polyphenols in accordance with the present invention is quite suitable for their analysis.

Polyphenols to be analyzed in the present invention are not restricted in particular. Examples thereof include substituted or unsubstituted divalent phenol or trivalent phenol, and the like. Among them, substituted or unsubstituted catechols and/or catechins having at least two hydroxyl groups, such as (+)-catechin (3,3',4',5,7-pentaoxyf lavan) or the like, for example, may be mentioned.

Labeling Reagent

The labeling reagent used in the present invention has a pyrene group. Here, the pyrene group includes unsubstituted pyrene rings and substituted pyrene rings. Though the substituents of the substituted pyrene rings are not limited in particular, those having a higher efficiency of labeling reaction for bisphenols and polyphenols and those having substituents not inhibiting the fluorescent derivative corresponding to bisphenols or polyphenols from forming the intramolecular excimer or substituents accelerating the intramolecular excimer formation can preferably be used.

The structure of the labeling reagent is not restricted in particular as long as it has a pyrene group. Therefore, it is possible to employ various pyrene-containing labeling reagents generally used for labeling oxyphenyl groups. As such a labeling reagent, for example, one expressed by the following formula (7) is preferably noted:

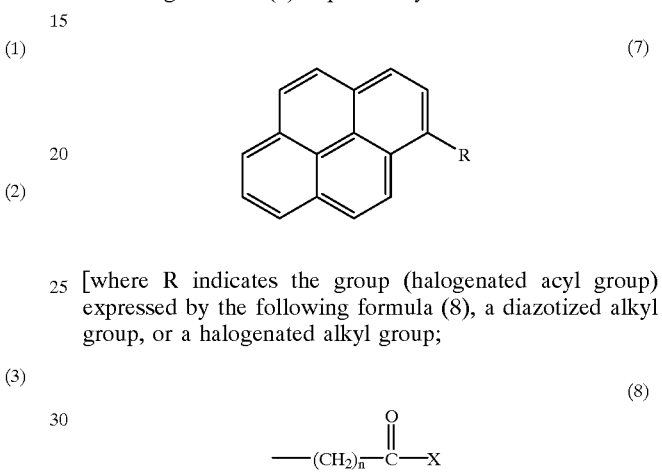

[where R indicates the group (halogenated acyl group) expressed by the following formula (8), a diazotized alkyl group, or a halogenated alkyl group;

$$-(CH_2)_n-\overset{O}{\underset{\|}{C}}-X \quad (8)$$

where X indicates a halogen element, and n indicates an integer of 1 or greater.]

Specific examples of the labeling reagent expressed by the above-mentioned formula (7) include 1-pyrene diazomethane in which the group R is —CHN$_2$, and 1-bromomethyl pyrene in which the group R is —CH$_2$BR. In formula (8), n is preferably at least 1 from the viewpoint of yielding a high efficiency in the labeling reaction so as to accelerate the generation of the fluorescent derivative, thus being able to improve the emission efficiency of the excimer fluorescence, whereas n is preferably 30 or less from the viewpoint of the solubility or dispersibility into solution samples or the industrial usability, and n within the range of 3 to 5 is particularly preferable. As such a labeling reagent, 4-(1-pyrene) butanoyl chloride expressed by the following formula (9) or 4-(1-pyrene) hexanoyl chloride is preferably used, for example.

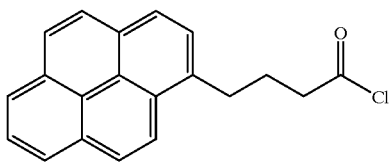

(9)

The labeling reagent is not limited to one having such a reaction selectivity that it preferentially reacts with terminal oxyphenyl groups, but may be one reacting with intramolecular oxyphenyl groups. Also, these oxyphenyl group labeling reactions may coexist. Therefore, polyphenols may be labeled with three or more pyrene groups depending on their structure. Even in such a case, as will be mentioned later, an intramolecular excimer is formed by two pyrene groups within the molecule of the fluorescent derivative, whereby excimer fluorescence can be observed.

The amount of the labeling reagent added to the test sample is such that it is sufficient for labeling bisphenols and/or polyphenols contained in the test sample. Though the labeling reagent added in excess coexists in the test solution while in an unreacted or hydrolyzed state, it is not necessary to separate and eliminate this excess labeling reagent in particular, since no excimer can be formed within the molecule and whereby no excimer fluorescence occurs.

For capturing acid components generated by the fluorescent derivative formation reaction, it is desirable that various bases be added together with the labeling reagent. Such an addition of bases restrains the occurring acid components from inhibiting the fluorescence emission from the fluorescent derivative, thus enhancing the fluorescence emission intensity. Examples of these bases include metal salts of inorganic weak acids, alkali compounds, amino compounds, and the like. Specifically, potassium carbonate, sodium acetate, quinuclidine, pyridine, sodium hydroxide, sodium carbonate, triethylamine, sodium hydrogencarbonate, and the like can be used. They can appropriately be selected according to the liquidity of the test sample, the kinds of bisphenols or polyphenols contained therein, and the like.

The reaction temperature in the fluorescent derivative formation is preferably 40 to 120° C., more preferably 80 to 100° C. If this temperature is less than 40° C., then there is a tendency of the fluorescent derivative formation reaction to become harder to advance remarkably. If this temperature exceeds 120° C., on the other hand, then it may become easier for the resulting fluorescent derivative to decompose depending on the reagent, while it becomes more difficult to use water, which is a polar solvent, or the like under a normal pressure.

Here, the above-mentioned excimer fluorescence is strongly observed in a polar solvent containing water in particular. It is presumed to be because of the fact that, in a water-containing polar solvent, for example, pyrene aromatic rings are located close to each other due to a hydrophobic mutual action. Due to such an action, the intensity of excimer fluorescence from the fluorescent derivative depends on the composition of the solvent (the water content, and the kind and ratio of existence of the polar solvent).

Amines

As mentioned above, the labeling reagent added to the test solution in excess does not generate excimer fluorescence, thereby reducing the possibility of inhibiting the excimer fluorescence in the present invention from being detected. For further enhancing the sensitivity in detecting the excimer fluorescence or separating the respective fluorescent derivatives corresponding to a plurality of kinds of bisphenols and/or polyphenols from each other by HPLC as mentioned above, it is preferred that the labeling reagent be decomposed.

In the present invention, it will be useful if amines having a polarity are used for decomposing the above-mentioned labeling reagent having a pyrene group. These amines are not restricted in particular as long as they have a polar group within their molecule. Specific preferable examples include amidosulfonic acids such as taurine, aliphatic amino acids such as arginine and γ-aminolactic acid, amino sugars such as glucosamine and mannosamine, and the like. Here, taurine is preferably used from the viewpoint of its high reagent purity and availability.

It has been confirmed here that, for example, when 4-(1-pyrene) butanoyl chloride expressed by formula (9) is used as the labeling reagent, while taurine is used as an amine, then the excess labeling reagent is decomposed into Pyren-$CH_2CH_2CH_2CONH$—$CH_2CH_2$—$SO_3^-$(where Pyren indicates a pyrene group). Upon determination of the fluorescence intensity before and after the amine addition, it has been confirmed that the fluorescence intensity after the addition is weaker than that before the addition.

Though the labeling reagent generates no intramolecular excimer as mentioned above, there is a possibility of an intermolecular excimer being formed. Though the fluorescence from the intermolecular excimer does not greatly influence the analysis of the intramolecular excimer fluorescence, it may become a factor causing background fluorescence. In the above-mentioned decomposition product, it is presumed that the formation of intermolecular excimer is inhibited by the electric repulsion due to $SO_3^-$, whereby the fluorescence emission from the intermolecular excimer is weakened.

Fluorometry

The fluorometric apparatus usable in the present invention is not limited in particular as long as it comprises a light source adapted to emit excitation light (preferably having a wavelength of 345 nm) for exciting the pyrene group and a fluorescence detector sensitive to excimer fluorescence (preferably having a wavelength of 475 nm) from the fluorescent derivative. Also, there is no particular restriction concerning the suitable concentration of bisphenols and/or polyphenols in the test sample, analyzing cell, and analyzing conditions, whereby usually known fluorescence observation conditions, devices, optical instruments, and the like can preferably be used. If necessary, a normally known method can optimize the fluorescence observation conditions.

In an example of specific fluorescence detection method, a potassium carbonate solution and 4-(1-pyrene) butanoyl chloride dissolved in a solvent such as acetonitrile are added to a test sample solution containing a bisphenol mixture, they are reacted for a predetermined period of time at a predetermined temperature so as to form a label, taurine and the like are added thereto, and the resulting solution is contained in a quartz cell having a volume on the order of 1 to 4 ml. The solution within this quartz cell is irradiated with excitation light having a wavelength of 345 nm, and fluorescence having a wavelength of 475 nm is detected as an analyzing wavelength.

Here, the intensity of the fluorescence having a wavelength of 450 to 530 nm is integrated, so as to yield the intensity of excimer fluorescence. While the fluorescence of the reagent blank has a maximum near a wavelength of 375 nm, near a wavelength of 395 nm, or the like, the intensity of the region having a wavelength longer than 450 nm is quite low. Also, if the solution having generated the fluorescent derivative is introduced into an HPLC so as to carry out the component separation, the contribution of the fluorescence resulting from the various reagents in the eluate and the impurities contained in the sample can be reduced to such an extent that it is negligible.

Method of Calculating Amount of Bisphenols or Polyphenols

The method of calculating (quantitatively determining) the amount of bisphenols and/or polyphenols in the test sample is based on the obtained excimer fluorescence intensity and the relationship between a known concentration of bisphenols or polyphenols in a standard sample and its fluorescence intensity. Specific examples include two methods set forth in the following, which are not limitative.

(1) Method by Calibration Curve

A standard sample containing a known concentration of bisphenols or polyphenols (available from Wako Pure Chemical Industries, Ltd. or the like) is used for carrying out the above-mentioned labeling reaction, and a calibration curve is prepared from the excimer fluorescence intensity obtained by the fluorometry and its corresponding concentration. With the excimer fluorescence intensity of the test sample being applied to thus prepared calibration curve, the total amount of bisphenols and/or polyphenols or the respective amounts of individual components (when separated by HPLC or the like) can be calculated.

(2) Method by Standard Addition

After a standard sample containing a known concentration of bisphenols or polyphenols is added to a test sample, a labeling reaction is carried out for the resulting solution, and the excimer fluorescence intensity is determined. When thus determined value is compared with the determined value of the excimer fluorescence intensity obtained without adding the above-mentioned standard sample, the amount of the bisphenols and/or polyphenols in the test sample can quantitatively be determined. The difference between the two determined values indicates the fluorescence emission intensity resulting from the standard sample having the known concentration, whereby this method is also one of quantitative determination methods based on the relationship between the standard sample having the known concentration of bisphenols or polyphenols and its fluorescence intensity.

Further, in the case where the fluorescence caused by the intramolecular excimer differs from the fluorescence of the pyrene group itself emitted without excitation light or excimer formation and the like in terms of the time and duration of emission, the decay of fluorescence after the excitation light irradiation may be determined. If the fluorescence intensity corresponding to the emission of the excimer fluorescence is integrated with respect to time in thus obtained fluorescence decay curve, the fluorescence resulting from bisphenols and/or polyphenols can be determined selectively with a high sensitivity. The emission of excimer fluorescence is on the order of several tens to one hundred and several tens of nanoseconds, so that determination with a sufficient time resolution can be effected with normal detection means.

In the embodiment of the method of analyzing bisphenols and polyphenols in accordance with the present invention explained in the foregoing, the labeling reagent substitutes for hydrogen atoms in phenolic hydroxyl groups in the molecule of bisphenols and/or polyphenols, whereby the fluorescent derivative labeled with the pyrene group is generated efficiently.

When this f luorescent derivative is irradiated with excitation light, the two pyrene groups within the molecule are optically excited. These excited monomer portions (excited pyrene groups) associate, thereby forming an excited dimer, i.e., excimer, within the molecule. Since this excimer occurs within a single molecule, the intensity of the fluorescence emitted from the excimer is monotonously proportional to the concentration of the fluorescent derivative molecule, i.e., the molecular concentration of bisphenols and/or polyphenols. Therefore, by determining such fluorescence intensity and using the above-mentioned calibration curve, the amount of bisphenols or polyphenols in the test sample can be calculated with a quantitative characteristic.

Also, when a reagent having a pyrene group is employed as the labeling agent, it is presumed to become easier to keep a structure of spatial configuration preferable for forming the excimer, so that the intramolecular excimer is favorably formed and held, whereby fluorescence can be detected stably. This tendency can be enhanced in particular when a labeling reagent having an unsubstituted pyrene ring is employed.

Further, when fluorescence having a wavelength specific to the intramolecular excimer is detected, then it can be determined as being discriminated from the fluorescence from the pyrene group itself or the monophenols and amines contained in the test sample. Therefore, the selectivity for bisphenols and/or polyphenols is enhanced, while the influence of background fluorescence can be reduced remarkably. Hence, the analysis with a high sensitivity and high accuracy is possible.

Furthermore, since the intramolecular excimer derives from the pyrene group acting as a labeling factor, the intensity of the fluorescence emitted from such an intramolecular excimer hardly depends on the kinds of bisphenols and/or polyphenols, i.e., their chemical structures. As a consequence, the total amount of a plurality of kinds of bisphenols or polyphenols contained in the test sample can be determined quite easily. If a test solution having generated a fluorescent derivative is introduced into HPLC or the like so as to separate components, then the respective amounts of bisphenols or polyphenols can easily be determined quantitatively.

Moreover, when the above-mentioned amines are added to a test solution containing a labeling reagent, the excess labeling reagent is decomposed, and the decomposition product is restrained from forming the intramolecular excimer, whereby the sensitivity for detecting fluorescence from the intramolecular excimer is further enhanced. Therefore, the sensitivity for analyzing bisphenols and/or polyphenols can further be enhanced. Here, if separation analysis by concurrent use of HPLC is carried out, then the eluting rate of the decomposition product is increased, whereby the separation between the fluorescent derivative and the decomposition product can be enhanced. Therefore, a mobile phase which can elute fluorescent derivatives faster can be employed, so that separations of the individual fluorescent derivatives corresponding to bisphenols and/or polyphenols can be improved. It is also advantageous in that, even without chromatography, the fluorescent derivative and the excess reagent can easily be separated from each other in the solid-phase extraction of reversed phase distribution type, for example.

EXAMPLES

In the following, the present invention is specifically explained with reference to Examples, which do not restrict the present invention as long as the latter does not deviate from the gist thereof.

Examples 1 to 6

Respective test sample solutions containing, as bisphenols, single materials of those expressed by formulas (1) to (6) (hereinafter referred to as "bisphenol A," "bisphenol B," "bisphenol E," "bisphenol F," "bisphenol AP," and "bisphenol P," respectively) by a concentration of 200 nmol/L were prepared; 200 $\mu$L of each of these test sample solutions were mixed with 10 $\mu$L of a 1 mol/L potassium carbonate solution and 200 $\mu$L of acetonitrile containing 4-(1-pyrene) butanoyl chloride at a concentration of 5 mmol/L; and the mixture was reacted at 100° C. for about 30 minutes, so as to effect labeling. After the completion of the labeling reaction, 10 $\mu$L of 100 mmol/L taurine were added to the test sample solution, and the resulting mixture was left for 5 minutes at room temperature.

Subsequently, a part of the test sample solution was dispensed and subjected to fluorometry with excitation light having a wavelength of 345 nm. FIG. 1 is a graph showing a fluorescent spectral curve of the test sample solution including a fluorescent derivative corresponding to bisphenol A ("a. u." on the ordinate of the graph indicating an arbitrary unit; ditto for the following). From the graph, it has been confirmed that excimer fluorescence is emitted in the wavelength range of 450 to 530 nm on the longer wavelength side from the fluorescence maximum (about 375 nm and about 395 nm) of the reagent blank.

Figure 2:
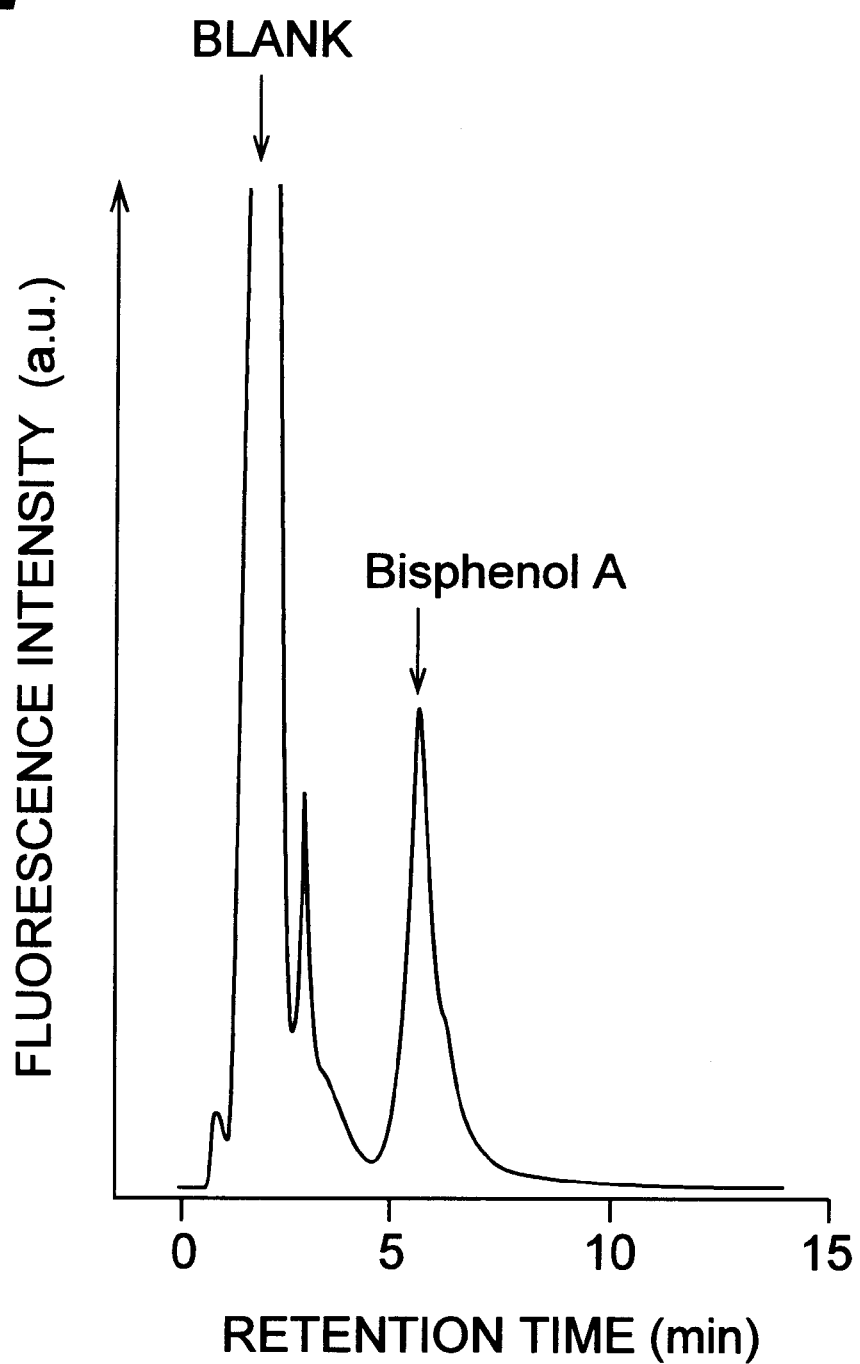
FIG. 2 shows a chromatogram of the test sample solution including the fluorescent derivative corresponding to bisphenol A.

On the other hand, 20 μL of each test sample solution was dispensed and introduced into HPLC (conditions: column of YMC-Pack TMS (inside diameter of 4.6 mm×height of 15 cm; manufactured by YMC, Inc.); mobile phase made of isocratic elution of acetonitrile/water (with a volume ratio of 3:1); and flow rate of 1 mL/minute), so as to separate fluorescent derivatives corresponding to the bisphenols. The eluate was irradiated with excitation light having a wavelength of 345 nm, and the excimer fluorescence having a wavelength of 475 nm was detected. FIG. 2 shows a chromatogram of the test sample solution including a fluorescent derivative corresponding to bisphenol A. From the chromatogram, it has been confirmed that, in the HPLC under the above-mentioned conditions, the fluorescent derivative corresponding to bisphenol A is detected after about 6.5 minutes and is fully distinguishable from the fluorescence of the reagent blank.

Figure 3:
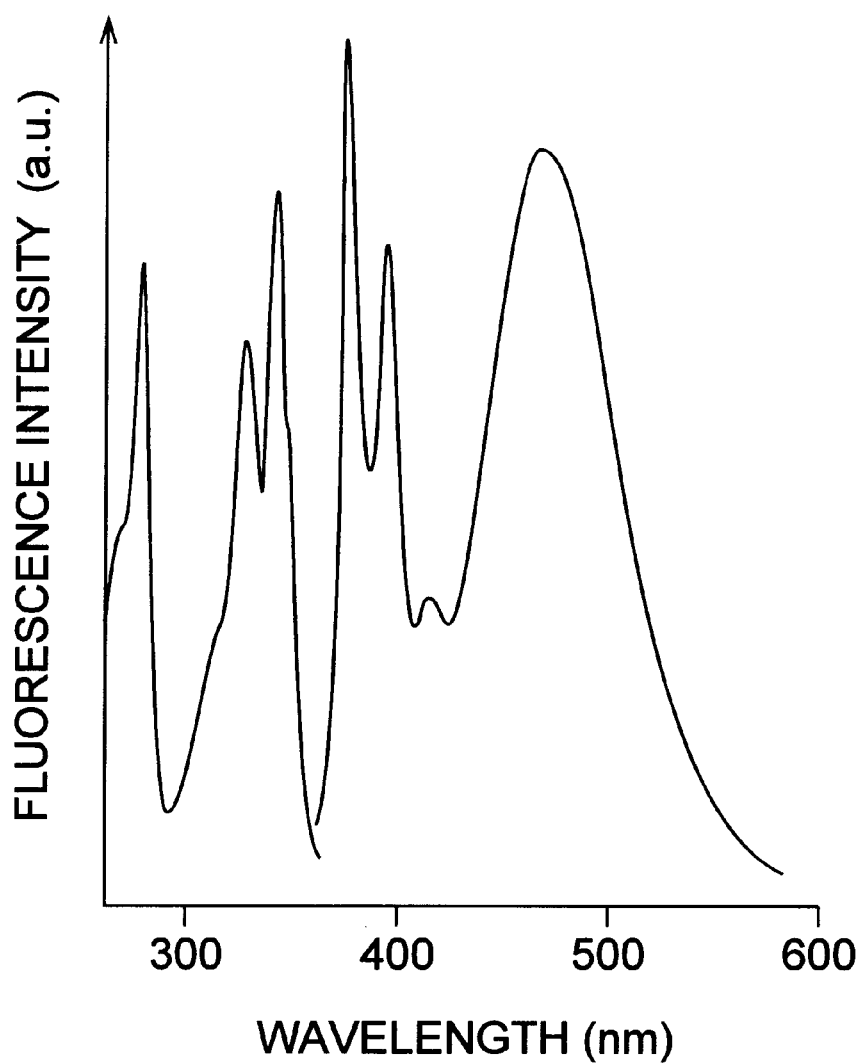
FIG. 3 is a graph showing a fluorescent spectral curve of an HPLC eluate mainly containing a fluorescent derivative corresponding to bisphenol A.

Also, an eluate mainly containing a fluorescent derivative corresponding to bisphenol A was fractionated and was irradiated with excitation light having a wavelength of 345 nm, so as to carry out fluorometry. FIG. 3 is a graph showing a fluorescent spectral curve of the HPLC eluate mainly containing a fluorescent derivative corresponding to bisphenol A. From the graph, the excimer fluorescence in the wavelength region of 450 to 530 nm has remarkably been confirmed.

Figure 4:
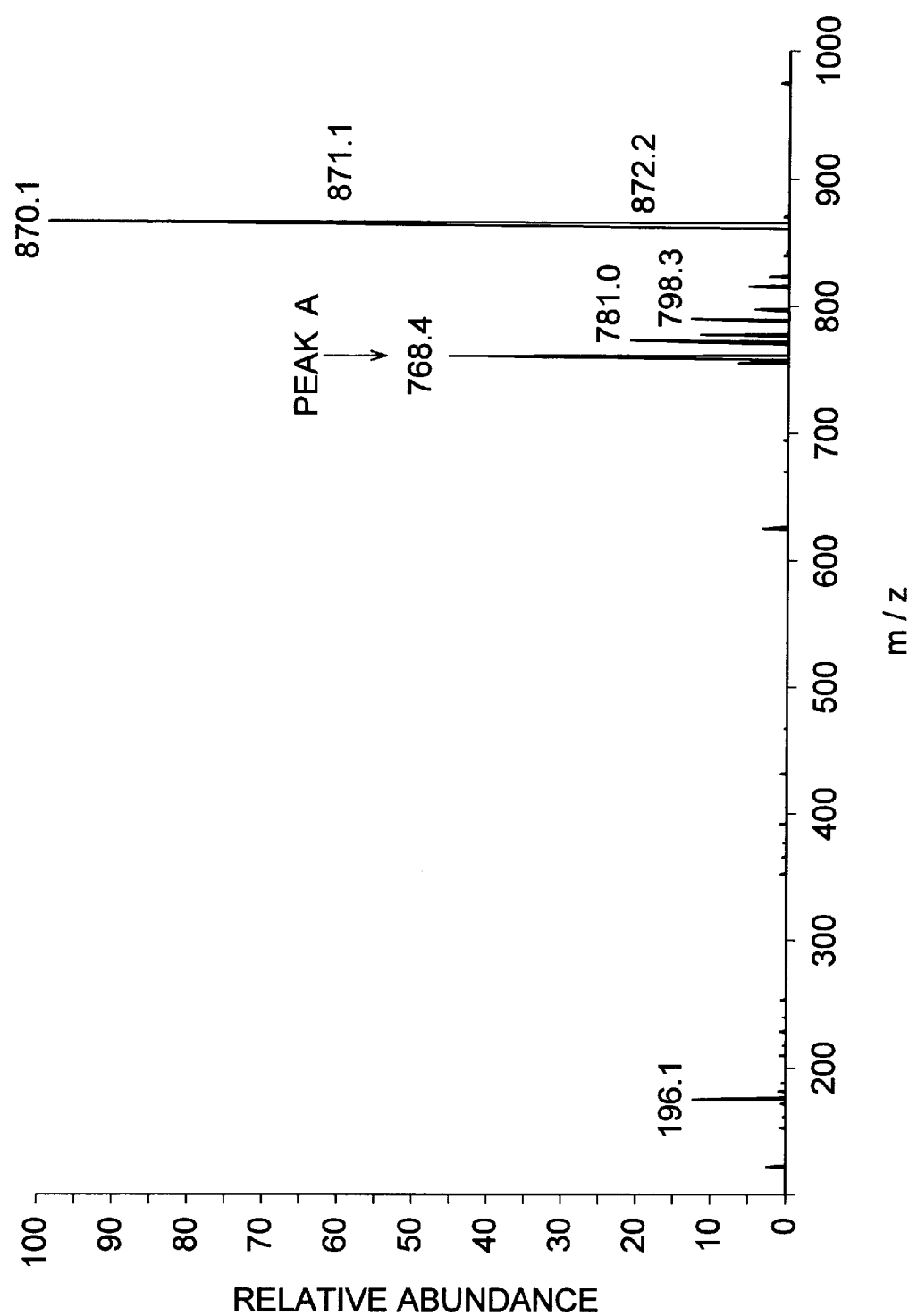
FIG. 4 is a graph showing a mass spectrum chart (mass spectrum) for a solution containing a fluorescent derivative corresponding to bisphenol A.

Further, each of the respective fluorescent derivatives of bisphenols separated by HPLC using a 10 mmol/L of acetic acid/triethylamine buffer (having a pH of 7.0) as the above-mentioned mobile phase in place of water was subjected to mass spectrometry (APCI-MS, manufactured by Finnigan Corporation, apparatus name: LCQ). As a result, it was seen that all the fluorescent derivatives were labeled at two positions within their molecule. FIG. 4 is a graph showing a mass spectrum chart (mass spectrum) for a solution containing a fluorescent derivative corresponding to bisphenol A. From the peak indicated by peak A (m/z=768.4) and the peak (m/z=870.1; the peak indicating the maximum intensity in the graph) corresponding to the molecular weight including triethylamine and H⁺ added thereto in this graph, it has been confirmed that the generated fluorescent derivative is the fluorescent derivative (having a molecular weight of about 768.3) of bisphenol A expressed by the following formula (10).

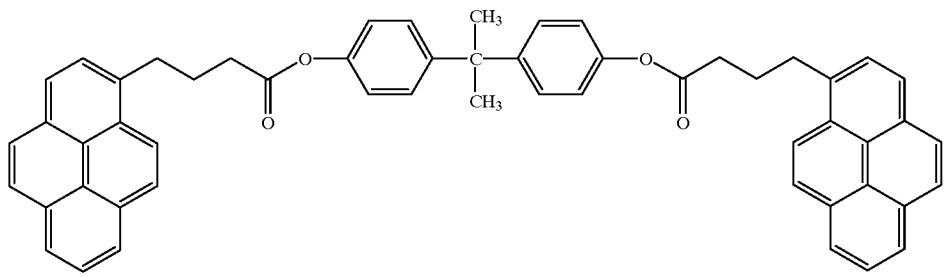

(10)

Example 7

The labeling reaction of the test sample solution, its fluorometry, and the fluorometry after its HPLC separation were carried out in a manner similar to the above-mentioned Examples 1 to 6 except that the test sample employed contained (+)-catechin as polyphenols. As a result, excimer fluorescence in the wavelength region of 450 to 530 nm was observed as with the case shown in FIGS. 1 and 3.

Example 8

Labeling was carried out in a manner similar to the above-mentioned Examples 1 to 6 except that a solution in which 40 μL each (200 μL in total) of respective test samples containing single products of bisphenol A, bisphenol B, bisphenol E, bisphenol F, and bisphenol AP (each having a concentration of 200 nmol/L) had been mixed was used as a test sample solution, and then it was subjected to fluorometry as it was, so as to yield its fluorescence intensity.

Further, this mixture was subjected to separation by HPLC, and the excimer fluorescence intensities based on the respective peaks of the fluorescent derivatives corresponding to the individual bisphenols were determined, whereby the fluorescence intensity (integrated value) of each component was obtained. The sum of the fluorescence intensities of individual components was found to be the same value (with a coefficient of variation of 5%) as the fluorescence intensity obtained for the solution before the above-mentioned HPLC separation. As a result, it has been confirmed that, in the present invention, the intensity of excimer fluorescence based on the pyrene group of the fluorescent derivatives derived from these bisphenols having different structures is substantially the same.

Preparation of Calibration Curve

Figure 5:
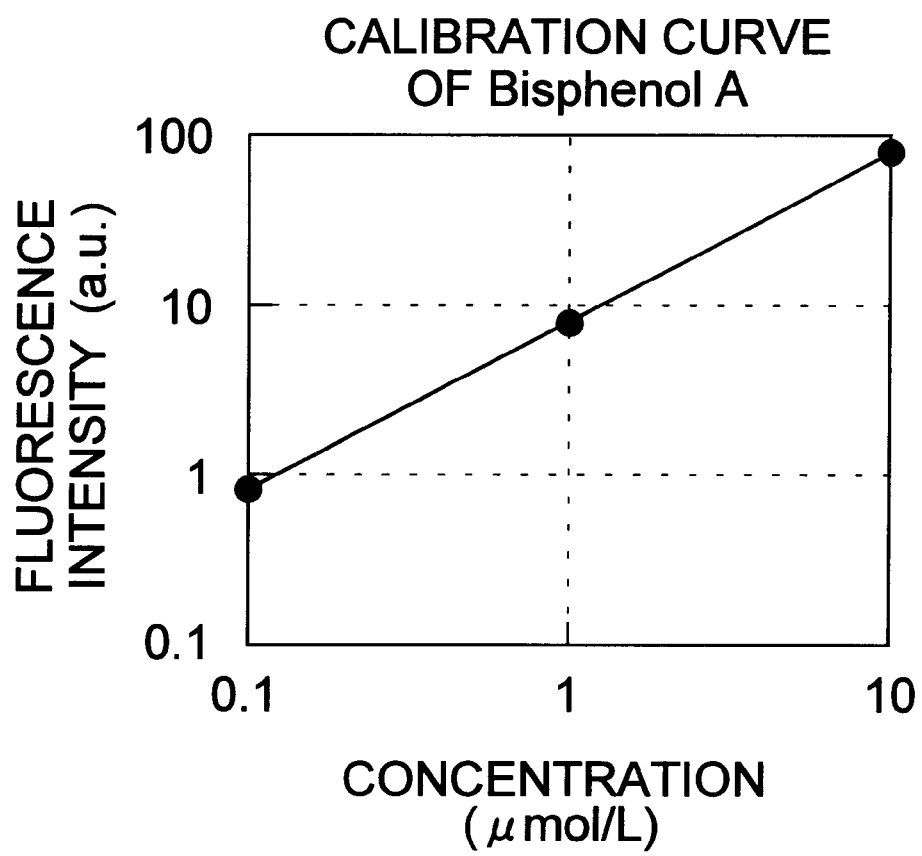
FIG. 5 is a graph showing a calibration curve (working curve) for a standard solution containing a fluorescent derivative corresponding to bisphenol A.

For respective standard solutions containing single products of bisphenol A, bisphenol B, bisphenol E, bisphenol F, bisphenol AP, bisphenol P, and (+)-catechin at concentrations of 0.1, 1, and 10 μmol/L, the fluorescence emitted from the fluorescent derivative corresponding to each component was determined as with the above-mentioned Examples 1 to 6, and calibration curves were prepared. FIG. 5 shows an example of calibration curves. FIG. 5 is a graph showing a calibration curve for a standard solution containing the fluorescent derivative corresponding to bisphenol A.

From this graph, it can be seen that this calibration curve has an excellent linearity, whereby the amount of bisphenols and/or polyphenols can be calculated with an excellent quantitative characteristic by using such a calibration curve. The respective calibration curves for bisphenols and (+)-catechin were substantially identical to each other. As a consequence, it can be seen that the total amount of the mixture of various bisphenols and/or polyphenols contained in a test sample can be determined easily and accurately. Further, by using separation means such as HPLC with respective calibration curves for single components, determination can be effected with a higher sensitivity.

Detection Limit, Reproducibility in Analysis, Etc.

The following Table 1 shows, for each of the bisphenols in the above-mentioned Examples 1 to 6, the HPLC retention time and the results of calculation of detection limit (3 $\sigma$ detection limit) at S/N=3. Also, as an index for reproducibility in analysis, the relative standard deviation (%) obtained after repeating the same analyzing operation six times is also indicated in Table 1. Here, the detection limit shown in the table is expressed by the number of moles per 20 $\mu$L of the test sample solution injected. From these results, it has been confirmed that any of bisphenols can be determined with a high sensitivity by a very small amount, while yielding a very high reproducibility.

TABLE 1

| Bisphenols | Retention time (min) | Detection limit (fmol) | RSD (%) (n = 6) |
|---|---|---|---|
| Bisphenol A | 6.6 | 3.5 | 2.2 |
| Bisphenol B | 7.1 | 3.6 | 3.9 |
| Bisphenol E | 6.1 | 5.4 | 2.4 |
| Bisphenol F | 5.9 | 4.6 | 3.7 |
| Bisphenol AP | 7.2 | 7.3 | 3.2 |
| Bisphenol P | 9.2 | 5.0 | 4.7 |

In the present invention, as explained in the foregoing, bisphenols and/or polyphenols are labeled with a labeling reagent having a pyrene group, so as to yield a fluorescent derivative; the emission of fluorescence having a wavelength specific to an intramolecular excimer formed upon irradiation of the fluorescent derivative with excitation light is detected; and, from the fluorescence intensity thereof, the amount of bisphenols and/or polyphenols is calculated. Therefore, according to the method of analyzing bisphenols and polyphenols in accordance with the present invention, bisphenols and/or polyphenols can be analyzed with a high sensitivity and a high selectivity. Also, without necessitating complicated preprocessing, bisphenols and/or polyphenols can be analyzed with a very high accuracy and good reproducibility.

What is claimed is:

1. A method of analyzing polyphenols and bisphenols for analyzing a polyphenol and/or a bisphenol having at least two phenolic hydroxyl groups contained in a test sample, said method comprising:

a step of reacting said bisphenol and/or said polyphenol with a labeling reagent having a pyrene group, so as to generate a fluorescent derivative;

a step of irradiating said fluorescent derivative with excitation light and detecting fluorescence emitted from said fluorescent derivative;

a step of calculating an amount of said bisphenol and/or said polyphenol in said test sample according to an intensity of thus detected fluorescence and a relationship between a known concentration of a bisphenol and/or a polyphenol contained in a standard sample and fluorescence intensity.

2. A method of analyzing polyphenols and bisphenols according to claim 1, wherein fluorescence having a wavelength of 450 to 530 nm is detected in said step of detecting fluorescence.

3. A method of analyzing polyphenols and bisphenols according to claim 1, wherein, as said test sample, one containing a bisphenol having an oxyphenyl group at a terminal within a molecule thereof is used.

4. A method of analyzing polyphenols and bisphenols according to claim 3, wherein said bisphenol is at least one selected from the group consisting of 2,2-bis(4-hydroxyphenyl) propane, 2,2-bis(4-hydroxyphenyl) butane, 4,4'-ethylidene bisphenol, bis(4-hydroxyphenyl) methane, 4,4'-(1-phenylethylidene) bisphenol, and 4,4'-(1,4-phenylene-di-isopropylidene) bisphenol.

5. A method of analyzing polyphenols and bisphenols according to claim 1, further comprising a step of adding an amine having a polar group to said test sample having generated said fluorescent derivative.

6. A method of analyzing polyphenols and bisphenols according to claim 5, wherein an amidosulfonic acid, aliphatic amino acid, or amino sugar is used as said amine.

7. A method of analyzing polyphenols and bisphenols according to claim 6, wherein said amine is at least one selected from the group consisting of taurine, arginine, γ-aminolactic acid, glucosamine, and mannosamine.

8. A method of analyzing polyphenols and bisphenols according to claim 1, wherein said labeling reagent having the pyrene group is at least one selected from the group consisting of 4-(1-pyrene) butanoyl chloride, 4-(1-pyrene) pentanoyl chloride, and 4-(1-pyrene) hexanoyl chloride.

* * * * *